(12) United States Patent
Faull et al.

(10) Patent No.: US 6,911,465 B1
(45) Date of Patent: Jun. 28, 2005

(54) ANTI-INFLAMMATORY INDOLE DERIVATIVES

(75) Inventors: Allan W Faull, Macclesfield (GB); Jason Kettle, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/889,515

(22) PCT Filed: Jan. 31, 2000

(86) PCT No.: PCT/GB00/00260

§ 371 (c)(1),
(2), (4) Date: Oct. 10, 2001

(87) PCT Pub. No.: WO00/46195

PCT Pub. Date: Aug. 10, 2000

(30) Foreign Application Priority Data

Feb. 5, 1999 (GB) ............................................. 9902459

(51) Int. Cl.$^7$ .................... A61K 31/405; C07D 209/04; A61P 291/001
(52) U.S. Cl. ....................................... 514/419; 548/492
(58) Field of Search ........................... 514/419; 548/492

(56) References Cited

U.S. PATENT DOCUMENTS

| | | |
|---|---|---|
| 3,557,142 A | 1/1971 | Bell |
| 3,776,923 A | 12/1973 | Remers et al. |
| 3,997,557 A | 12/1976 | Helsley et al. |
| 4,384,994 A | 5/1983 | Verber et al. |
| 4,529,724 A | 7/1985 | Ho |
| 4,721,725 A | 1/1988 | Biller et al. |
| 4,751,231 A | 6/1988 | Halczenko et al. |
| 4,965,369 A | 10/1990 | Maetzel et al. |
| 5,081,145 A | 1/1992 | Guindon et al. |
| 5,145,845 A * | 9/1992 | Johnson et al. |
| 5,190,968 A | 3/1993 | Gillard et al. |
| 5,254,563 A | 10/1993 | Huth et al. |
| 5,272,145 A | 12/1993 | Prasit et al. |
| 5,273,980 A | 12/1993 | Frenette et al. |
| 5,288,743 A | 2/1994 | Brooks et al. |
| 5,290,798 A | 3/1994 | Gillard et al. |
| 5,308,850 A | 5/1994 | Gillard et al. |
| 5,389,650 A | 2/1995 | Frenette et al. |
| 5,399,699 A | 3/1995 | Kolasa et al. |
| 5,482,960 A | 1/1996 | Berryman et al. |
| 5,604,253 A | 2/1997 | Lau et al. |
| 5,639,780 A | 6/1997 | Lau et al. |
| 5,684,032 A | 11/1997 | Elliott et al. |
| 5,852,046 A | 12/1998 | Lang et al. |
| 5,877,199 A | 3/1999 | Birdsall et al. |
| 5,955,492 A | 9/1999 | Thompson et al. |
| 6,184,235 B1 | 2/2001 | Connor et al. |

FOREIGN PATENT DOCUMENTS

| | | |
|---|---|---|
| DE | 298 913 A5 | 3/1992 |
| EP | 0 189 690 | 8/1986 |
| EP | 0 419 049 A1 | 3/1991 |
| EP | 0 480 659 A2 | 4/1992 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 573 A1 | 2/1995 |
| EP | 0 822 185 | 2/1998 |
| EP | 0 275 667 | 7/1998 |
| FR | 2 565 981 | 12/1985 |
| JP | 63284177 | 11/1988 |
| JP | 4273857 | 9/1992 |
| WO | WO 86 00896 | 2/1986 |
| WO | WO 92 04343 | 3/1992 |
| WO | WO 93/12780 | 7/1993 |
| WO | WO 93 16069 | 8/1993 |
| WO | WO 93/20078 | 10/1993 |
| WO | WO 94 14434 | 7/1994 |
| WO | WO 97/13615 | 4/1997 |
| WO | WO 97/30704 | 8/1997 |
| WO | WO 97/35572 | 10/1997 |
| WO | WO 98/06703 | 2/1998 |
| WO | WO 99/07351 | 2/1999 |
| WO | WO 99/07678 | 2/1999 |
| WO | WO 99/33800 | 7/1999 |

OTHER PUBLICATIONS

Krutosikova, A. et al. Condensed O–, X–Heterocycles by the Transformation of Azidoncrylates. *Chemical Monthly* 123. 807–815 (1992).

Krutosikova, A. et al. Derivatives of Furo[3.2–b]Pyrrole. *Collect. Czech. Chem. Commun.* 59. 473–481 (1994).

Krutosikova, A. et al. Substituted Vinyl Azides in the Synthesis of Condensed Nitrogen Heterocycles. *Chem. Papers* 48. 268–273 (1994).

Krutosikova, A. et al. Synthesis and Reactions of Furo[3.2b] Pyrrole Type Aldehydes. *Collect. Czech. Chem. Commune.* 58. 2139–2149 (1993).

(Continued)

*Primary Examiner*—Rita Desai
*Assistant Examiner*—Robert Shiao
(74) *Attorney, Agent, or Firm*—Ropes & Gray LLP

(57) ABSTRACT

Therapeutic compounds of formula (I) wherein X is $CH_2$ or $SO_2$; $R^1$ is an optionally substituted aryl or heteroaryl ring; $R^2$ and $R^3$ are various specified groups, $R^4$ is a group $NHCOR^{15}$, $NHSO_2R^{15}$ or $OCONR^{16}R^{17}$ where $R^{15}$, $R^{16}$ and $R^{17}$ are various defined groups; and $R^5$, $R^6$ and $R^7$ are independently selected from hydrogen, a functional group or an optionally substituted hydrocarbyl groups or optionally substituted heterocyclic groups; and further provided that when $R^4$ is a group $NHCOR^{15}$, $R^{15}$ is substituted alkyl, optionally substituted aryl or optionally substituted heteroaryl; as well as pharmaceutical compositions containing them are described and claimed. These compounds and compositions are useful in the treatment of disease mediated by MCP-1 (monocyte chemoattractant protein-1) or RANTES (Regulated Upon Activation, Normal T-cell Expressed and Secreted), such as inflammatory disease.

8 Claims, No Drawings

OTHER PUBLICATIONS

Krutosikova, A. et al. Synthesis and Reactions of Furo[2.3b] pyrroles. *Molecules* 2. 69–79 (1997).

Murakami, Y. et al. Direct Regioselective Vinylation of Indoles Using Palladium (II) Chloride. *Heterocycles* 22. 1493–1496 (1984).

Rosenmund, P. et al. Decarboxylations of Some 1–Alkyl–2–carboxy–3–indolocetic Acids and Synthesis of a 5–Thiocyanain–2.3–dihydroindole. *Chem. Ber.* 108, 3538–3542 (1975).—Abstract only.

Troschutz, R. & Hoffmann, A. Synthesis of Substituted 3–Amino–4–cyano–1–oxo–1,3,5,10–tetrahy–droazepino [3.4b]indoles. *J Heterocyclic Chem.* 34, 1431 (1997).

Yokoyama, Y. et al. Palladium–Catalyzed Cross–Coupling Reaction: Direct Allylation of Aryl Bromides with Allyl Acetate. *Tetrahedton Letters* 26, 6457–6460 (1985).

Yukoyama, Y. et al. New Synthetic Method for Dehydrotryptophan Derivatives. Synthesis Studies on Indoles and Related Compounds. XXIV. *Chem. Pharm. Bull.* 42, 832–838 (1994).

Organic Chemistry, 5$^{th}$ Edition, Fessenden and Fessenden, 1994, p. 790.*

Berman, J.W. et al, Localization of Monocyte Chemoattractant Peptide–1 Expression in the Central Nervous System in Experimental Autoimmune Encephalomyelitis and Trauma in the Rat. *J. Immunol.* 156, 3017–3023 (1996).

Bobosik, V. & Krutosikova, A. Synthesis of N–Phenylsulfonyl Protected Furo[3.2–b]Pyrroles *Collect. Czech. Chem. Commun.* 59, 499–502 (1994).

Dandarova, M. 13C NMR Spectra of Some Substituted Furo[3.2–b]pyrroles. *Magnetic Resonance Chem.* 28, 830–831 (1990).

Deleuran, M. et al. Localization of monocyte chemotactic and activating facton (MCAP/MCP 1) in psoriasis *J. Dermatological Sci* 13, 228–236 (1996).

Grimm, M.C. et al. Enhanced expression and production of monocyte chemoattractant protein–1 in inflammatory bowel disease mucosa. *J. Leukocyte Biol.* 59, 804–812 (Jun. 1996).

Harrison, C.–A. et al. Cyclopenta [b] indoles. Part 2. Model studies towards the tremorgenic mycotoxins. *J. Chem. Soc. Perkin Trans.* 1131–1136 (1995).

Hartman, G.D. & Halezenko, W. The Synthesis of 5–Alkylaminomethylthieno[2.3–b]pyrrole–5–sulfonamides. *Heterocycles* 29, 1943–1949 (1989).

Jones, M.I., et al. Potential Role of Monocyte Chemoattractant Protein EJE in Monocyte/Macrophage–Dependent IgA Immune Complex Aveolitis in the Rat. *J. Immunol* 149, 2147–2154 (Sep. 15, 1992).

Kataoka, K. et al. Homopiperazines as cell migration inhibitors. *Chemical Abstracts*. Columbus Ohio, US 123, 667 (Oct. 2, 1995).

Koch, A.E. et al. Enhanced Production of Monocyte Chemoattractant Protein–1 Rheumatoid Arthritis. *J. Clin. Invest.* 90, 772–779 (Sep. 1992).

Korobchenko, I.V. et al. Synthesis and antiviral activity of pyrrolecarboxylic acids and derivatives. *Chemical Abstracts* Columbus, Ohio Access Number 119 62465 (1999).

Krutosikova, A. & Dandarova. M. Substituted Vinyl Azides in Synthesis of Furo[3.2–b.4.5–b]–Dipyrroles and Pyrrolo [213.4.5]Furo[3.2–c]Pyridines. *Heterocycles* 37, 1695–1700 (1994).

Krutosikova. A. & Dandarova. M. Reactions of Methyl 2–Formylfuro[3.2–b]pyrrole–5–carboxylaes. *Chem Papers* 50,72–76, (1996).

* cited by examiner

ANTI-INFLAMMATORY INDOLE DERIVATIVES

The present invention relates to chemical compounds, to their production as well as to pharmaceutical compositions containing them as well as to their use in therapy, in particular of inflammatory disease.

MCP-1 is a member of the chemokine family of pro-inflammatory cytokines which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.,* 149, 2147) and astham. Other disease area where MCP-1 is thought to play a part in their pathology are atherosclerosis (e.g. Koch et al., 1992, *J. Clin. Invest.,* 90, 772–779), psoriasis (Deleuran et al., 1996, *J. Dermatological Science,* 13, 228–236), delayed-type hypersensitivity reactions of the skin, inflammatory bowel disease (Grimm et al., 1996, *J. Leukocyte Biol.,* 59,. 804–812), multiple sclerosis and brain trauma (Berman et al, 1996, *J. Immunol.,* 156,. 3017–3023). An MCP-1 inhibitor may also be useful to treat stroke, reperfusion injury, ischemia, myocardial infarction and transplant rejection.

MCP-1 acts through the MCP-1 receptor (also known as the CCR2 receptor). MCP-2 and MCP-3 may also act, at least in part, through the MCP-1 receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the MCP-1 receptor.

Copending International Patent Application Nos. PCT/GB98/02340 and PCT/GB98/02341 describe and claim groups of compounds based upon the indole ring structure which are inhibitors of MCP-1 and therefore have applications in therapy.

The use of certain indole derivatives as NMDA antagonists is described is U.S. Pat. No. 5,051,442, WO9312780, EP-483881. Other indoles and their use as inhibitors of leukotriene biosynthesis is described in for example, EP-A-275-667.

The applicants have found a particular substitution on the indole ring produces advantageous results when used therapeutically as inhibitors of MCP-1.

According to the present invention there is provided a compound of formula (I)

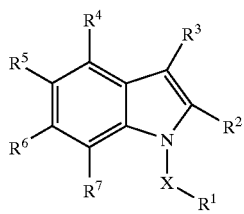

(I)

X is $CH_2$ or $SO_2$ $R^1$ is an optionally substituted aryl or heteroaryl ring;

$R^2$ is carboxy, cyano, —C(O)CH$_2$OH, —CONHR$^8$, —SO$_2$NHR$^9$, tetrazol-5-yl, SO$_3$H, or a group of formula (IV)

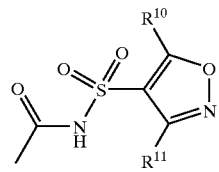

(VI)

where $R^8$ is selected from hydrogen, alkyl, aryl, cyano, hydroxy, —SO$_2$R$^{12}$ where $R^{12}$ is alkyl, aryl, heteroaryl, or haloalkyl, or $R^8$ is a group-(CH$^{13}$)$_3$—COOH where r is an integer of 1–3 and each $R^{13}$ group is independently selected from hydrogen or alkyl; $R^9$ is hydrogen, alkyl, optionally substituted aryl such as optionally substituted phenyl or optionally substituted heteroaryl such as 5 or 6 membered heteroaryl groups, or a group COR$^{14}$ where $R^{14}$ is alkyl, aryl, heteroaryl or haloalkyl; $R^{10}$ and $R^{11}$ are independently selected from hydrogen or alkyl, particularly $C_{1-4}$ alkyl;

$R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl;

$R^4$ is a group NHCOR$^{15}$, NHSO$_2$R$^{15}$ or OCONR$^{16}$R$^{17}$ where $R^{15}$ is optionally substituted alkyl, optionally substituted aryl or optionally substituted heteroaryl and $R^{16}$ and $R^{17}$ are independently selected from hydrogen, optionally substituted alkyl, optionally substituted aryl and optionally substituted heteroaryl, with the proviso that at least one of $R^{16}$ or $R^{17}$ is other than hydrogen, or $R^{16}$ and $R^{17}$ together with the nitrogen atom to which they are attached form an optionally substituted heterocyclic ring which optionally contains further heteroatoms; and $R^5$, $R^6$ and $R^7$ are independently selected from hydrogen, a functional group or an optionally substituted hydrocarbyl groups or optionally substituted heterocyclic groups.

Suitably, where $R^4$ is a group NHCOR$^{15}$, $R^{15}$ is substituted alkyl, optionally substituted aryl or optionally substituted heteroaryl.

Compounds of formula (I) are inhibitors of monocyte chemoattractant protein-1. In addition, they appear to inhibit RANTES (Regulated upon Activation, Normal T-cell Expressed and Secreted), induced chemotaxis. RANTES is another chemokine from the same family as MCP-1, with a similar biological profile, but acting through the CCR1 receptor. As a result, these compounds can be used to treat disease mediated by these agents, in particular inflammatory disease.

In this specification the term 'aryl' when used either alone or as a suffix includes straight chained, branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents. They may comprise electron-donating or electron-withdrawing. Examples of such groups include halo, cyano, nitro, $C(O)_nR^{18}$, $OR^{18}$, $S(O)_nR^{18}$, $NR^{19}R^{20}$, $C(O)NR^{19}R^{20}$, $OC(O)NR^{19}R^{20}$, $-NR^{19}C(O)_nR^{18}$, $-NR^{18}CONR^{19}R^{20}$, $-N=CR^{19}R^{20}$, $S(O)_mNR^{19}R^{20}$ or $-NR^{19}S(O)_mR^{18}$ where $R^{18}$, $R^{19}$ and $R^{20}$ are independently selected from hydrogen or optionally substituted hydrocarbyl, or $R^{19}$ and $R^{20}$ together form an optionally substituted ring which optionally contains further heteroatoms such as $S(O)_m$, oxygen and nitrogen, n is an integer of 1 or 2, m is 1 or 2.

Suitable optional substituents for hydrocarbyl groups $R^{18}$, $R^{19}$ and $R^{20}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_nR^2$ where n is as defined above and $R^8$ is alkyl such as $C_{1-4}$ alkyl.

Suitable substituents for these hydrocarbyl or heterocyclic groups include those listed above for $R^{18}$, $R^{19}$ and $R^{20}$.

Suitably $R^1$ is an optionally substituted phenyl, pyridyl, naphthyl, furyl or thienyl ring, and in particular is a substituent phenyl or pyridyl ring.

Suitable optional substituents for $R^1$ in formula (I) include alkyl, alkenyl, alkynyl, halo, haloalkyl including perhaloalkyl such as trifluoromethyl, mercapto, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, oximino, sulphonamido, carbamoyl, mono or dialkylcarbamoyl or $S(O)_mR^{21}$ where m is as defined above and $R^{21}$ is hydrocarbyl.

Particular examples of substituents $R^5$, $R^6$ and $R^7$, and where appropriate also $R^4$ include hydrogen, hydroxy, halo, optionally substituted alkyl such as aralkyl, carboxyalkyl or the amide derivative thereof; alkoxy; aryloxy; aralkyloxy; or an amino group which is optionally substituted with alkyl, aryl or aralkyl. A specific functional group which is suitable for $R^4$, $R^5$, $R^6$ and/or $R^7$ is a group of sub-formula (IV).

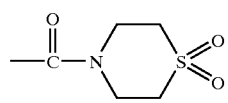

(IV)

Particular examples of groups $R^5$, $R^6$ and $R^7$ are hydrogen, hydroxy, halo or alkoxy. In particular $R^6$ and $R^7$ are hydrogen. $R^5$ may be hydrogen but in addition is suitably a small substituent such as hydroxy, halo or methoxy.

Particular substituents for $R^1$ include trifluoromethoxy, $C_{1-4}$alkyl, halo, trifluoromethoxy, $C_{1-4}$alkoxy, $C_{1-4}$alkanoyl, $C_{1-4}$alkanoyloxy, nitro, carbamoyl, $C_{1-4}$alkoxycarbonyl, $C_{1-4}$alkylsulphanyl, $C_{1-4}$alkylsulphinyl, $C_{1-4}$alkylsulphonyl, sulphonamido, carbamoyl$C_{1-4}$alkyl, N-($C_{1-4}$alkyl)carbamoyl$C_{1-4}$alkyl, N-($C_{1-4}$alkyl)$_3$carbamoyl-$C_{1-4}$alkyl, hydroxy$C_{1-4}$alkyl or $C_{1-4}$alkoxy$C_{1-4}$alkyl.

Additionally or alternatively, two such substituents together may form a divalent radical of the formula —O(CH$_2$)$_{1-4}$O— attached to adjacent carbon atoms on the $R^1$ ring.

Preferred substituents for $R^1$ are one or more non-polar substituents such as halo.

In particular, $R^1$ is substituted by one or more halo groups, in particular chlorine. A particular example of an $R^1$ group is 3,4-dichlorophenyl, 3,4-fluoro-4-chlorophenyl, 3-chloro-4-fluorophenyl or 2,3-dichloropyrid-5-yl.

Examples of groups $R^2$ include carboxy; cyano; tetrazol-5-yl; SO$_2$H; —CONHR$^8$ where $R^8$ is selected from cyano, hydroxy, —SO$_2$R$^{12}$ where $R^{12}$ is alkyl such as $C_{1-4}$ alkyl, aryl such as phenyl, heteroaryl or trifluoromethyl, or $R^8$ is a group-(CHR$^{10}$)$_r$—COOH where r is an integer of 1–3 and each $R^{10}$ group is independently selected from hydrogen or alkyl such as $C_{1-7}$ alkyl; or $R^2$ is a group —SO$_2$NHR$^9$ where $R^9$ is an optionally substituted phenyl or an optionally substituted 5 or 6 membered heteroaryl group, or a group COR$^{14}$ where $R^{14}$ is alkyl such as $C_{1-4}$alkyl, aryl such as phenyl, heteroaryl or trifluoromethyl, or $R^2$ is a group of formula (VI)

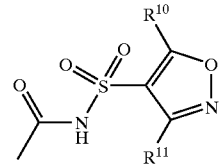

(VI)

where $R^{10}$ and $R^{11}$ are independently selected from hydrogen or alkyl, particularly $C_{1-4}$ alkyl.

Preferably $R^2$ is carboxy or a pharmaceutically acceptable salt or ester thereof.

Suitable groups $R^3$ include hydrogen, fluoro, chloro, bromo, iodo, methyl, cyano, trifluoromethyl, hydroxymethyl, alkoxyalkyl such as $C_{1-4}$alkoxymethyl, methoxy, benzyloxy, carboxyalkoxy such as carboxymethoxy, methylsulphanyl, methylsulphinyl, methylsulphonyl or carboxy$C_{3-6}$cycloalkyl, —(CHR$^{22}$)$_r$—NR$^{23}$R$^{24}$ (where r is 0–2, each $R^{22}$ is independently hydrogen or alkyl, in particular $C_{1-4}$ alkyl, $R^{23}$ and $R^{24}$ are independently selected from H and $C_{1-4}$alkyl or $R^{23}$ and $R^{24}$ together with the nitrogen to which they are attached form a 5 or 6 membered ring optionally containing one further heteroatom selected from O, N, S, S(O) or SO$_2$. Suitably $R^{23}$ and $R^{24}$ together form a heterocyclic ring such as morpholino or piperazinyl.

Other such groups $R^3$ include optionally substituted aryl groups, such as optionally substituted phenyl or naphthyl group. Suitable substituents for phenyl groups $R^3$ include one or more groups selected from chlorine, fluorine, methyl, trifluoromethyl, trifluoromethoxy, amino, formyl, phenyl, methoxy, phenoxy or phenyl.

$R^3$ may comprise a range of substituents as listed above, in particular, hydrogen or a small substituent group such as $C_{1-4}$alkyl in particular methyl, or trifluoromethyl, and is preferably hydrogen.

Suitable optional substituents for the group $R^{15}$, $R^{16}$ and $R^{17}$ as they appear in the definition of $R^4$, include functional groups as hereinbefore defined, as well as aryl or heterocyclyl groups, either of which may themselves be substituted by one or more functional groups or further aryl or heterocyclyl groups.

Particular examples of substituents for groups $R^{15}$, $R^{16}$ and $R^{17}$ include one or more groups selected from halo such as chloro; hydroxy; cyano; amino; mono- or di-alkylamino; $C_{1-4}$ alkoxy; carboxy; sulphonamido; $CONH_2$; alkylamido where the alkyl moiety is optionally substituted for example with a functional groups such as carboxy; morpholino; pyridyl; pyrimidinyl; phenyl optionally substituted by halo such as chloro, hydroxy, alkoxy such as methoxy, carbamoyl, acyl such as acetyl, or hydroxyalkyl where the alkyl group suitably includes at least two carbon atoms, such as hydroxyethyl. Other examples of substituents for phenyl groups $R^{15}$ is alkanoylamino group such as methoylamino.

Where $R^{15}$, $R^{16}$ and/or $R^{17}$ is a heterocyclyl group, or where $R^{16}$ and $R^{17}$ together form an optionally substituted heterocyclic ring, these may be substituted by functional groups such as halo or hydroxy, or by alkyl groups such as methyl or ethyl, or alkenyl or alkynyl groups any of which may be substituted, for example with hydroxy, as well as with further heteroaryl groups such as pyridyl. Particular examples of heterocyclic groups $R^{15}$, $R^{16}$ and/or $R^{17}$ are optionally substituted thiophenyl, optionally substituted imidazolyl, optionally substituted pyridyl.

Thus thiophenyl groups $R^{15}$, $R^{16}$ and/or $R^{17}$ may comprise pyridyl-thiophenyl, whilst an example of a substituted imidazolyl group for $R^{15}$, $R^{16}$ and/or $R^{17}$ is methylimidazolyl and halopyridyl in particular chloropyridyl is an example of a substituted pyridyl moiety for these groups.

Particular examples of $R^{15}$ include alkyl in particular methyl optionally substituted by a functional groups or, in particular, a heterocyclyl group where the heterocyclyl group may be optionally substituted by a functional group such as halo or hydroxy or by an alkyl group such as methyl. Preferably, $R^{15}$ is a substituted alkyl group. Where the substituent is a functional group, it is preferably a group of formula $NR^{19}R^{20}$ where $R^{19}$ and $R^{20}$ are as defined above. Thus examples of substituted alkyl groups $R^{15}$ include morpholinomethyl or alkyl such as methyl substituted with a substituted alkyl amino group wherein the substituents include carboxy, alkanoyl, phenyl or alkyl sulphonyl.

Other examples of $R^{15}$ are heterocylcyl groups which are optionally substituted for example by alkyl such as methyl, functional groups such as chloro or heterocycyl groups such as pyridyl.

Particular examples of $R^{16}$ and $R^{17}$ are alkyl such as methyl.

X is $CH_2$ or $SO_2$ and is preferably $CH_2$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include alkyl esters, such as $C_{1-6}$ alkyl esters for example, ethyl esters, $C_{1-6}$alkoxymethyl esters for example methoxymethyl, $C_{1-6}$alkanoyloxymethyl esters for example pivaloyloxymethyl, phthalidyl esters, $C_{1-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically acceptable esters of compounds of formula (I) are in vivo hydrolysable ester of a compound of the formula (I) containing a hydroxy group includes inorganic esters such as phosphate esters and α-acyloxyalkyl ethers and related compounds which as a result of the in-vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Esters which are not in vivo hydrolysable are useful as intermediates in the production of the compounds of formula (I) and therefore these form a further aspect of the invention.

Thus examples of compounds of formula (I) include the following:

TABLE 1

| Compd No. | $R^3$ | $R^4$ | $R^5$ | $R^6$ | $R^a$ | $R^b$ |
|---|---|---|---|---|---|---|
| 1 | H | pyridyl-thiophenyl-sulfonamide | H | H | H | H |
| 2 | H | morpholinyl-acetamide | H | H | Cl | Cl |
| 3 | H | piperazinyl-acetamide | H | H | Cl | Cl |

TABLE 1-continued

Structure: Indole with R³ at 3-position, R⁴ at 4-position, R⁵ at 5-position, R⁶ at 6-position, 2-COOH, N-benzyl with Rᵃ (3-position) and Rᵇ (4-position) on the phenyl.

| Compd No. | R³ | R⁴ | R⁵ | R⁶ | Rᵃ | Rᵇ |
|---|---|---|---|---|---|---|
| 4 | H | 4-(CH₃NHSO₂)-C₆H₄-NHC(O)- * | H | H | Cl | Cl |
| 5 | H | 5-(2-pyridyl)-thiophene-2-sulfonyl-N(CH₃)- * | H | H | Cl | Cl |
| 6 | H | (1,1-dioxo-thiomorpholin-4-yl)CH₂C(O)N(CH₃)- * | H | H | Cl | Cl |
| 7 | H | (1-methylimidazol-4-yl)-SO₂-N(CH₃)- * | H | H | Cl | Cl |
| 8 | H | NHC(O)CH₂NHCH₂COOH | H | H | Cl | Cl |
| 9 | H | 2-chloro-pyridine-5-sulfonyl-N(CH₃)- * | H | H | Cl | Cl |
| 10 | H | OC(O)N(CH₃)₂ | H | H | Cl | Cl |
| 11 | H | CH₃N(H)C(O)CH₂N(S(O)₂CH₃)CH₂COOH * | H | H | Cl | Cl |
| 12 | H | CH₃N(H)C(O)CH₂N(C(O)CH₃)CH₂COOH * | H | H | Cl | Cl |
| 13 | H | CH₃N(H)C(O)CH₂N(CH₂C₆H₅)CH₂COOH * | H | H | Cl | Cl |
| 14 | H | NHC(O)CH₂N(CH₃)CH₃COOH | H | H | Cl | Cl |
| 15 | H | CH₃N(*)C(O)CH₂N(CH₂C₆H₅)CH₂COOH | H | H | Cl | Cl | where * indicates the point of attachment of the group to the indole ring.

Compounds of formula (I) are suitably prepared by methods such as those described in International Patent Application Nos. PCT/GB98/02340 and PCT/GB98/02341.

In particular compounds of formula (I) where R⁴ is NHCOR¹⁵ or NHSO₂R¹⁵ can be prepared by reacting a compound of formula (VII)

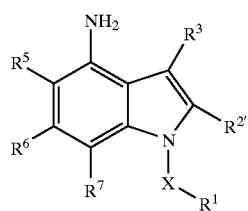

(VII)

where X, R¹, R³, R⁵, R⁶ and R⁷ are as defined in relation to formula (I), R²′ is a group R² as defined in relation to formula (I) or a protected form thereof, with a compound of formula (VIII)

$$Z—R^{22}$$ (VIII)

where Z is a leaving group and $R^{22}$ is a group $COR^{15'}$ or $SO_2R^{15'}$ where $R^{15'}$ is group $R^{15}$ as defined in relation to formula (I) or a precursor thereof;
and thereafter if desired or necessary:
(i) converting a precursor group $R^{15'}$ to a group $R^{15}$ and/or converting a group $R^{15}$ to a different such group;
(ii) deprotecting a group $R^{2'}$ to a group $R^2$.

Suitable leaving groups Z include halo such as chloro. The reaction is suitably effected in an organic solvent such as dichloromethane or tetrahydrofuran in the presence of a base such as triethylamine or pyridine. Moderate temperatures, for example from 0° to 50° C. and conveniently ambient temperature, are employed in the reaction.

Compounds of formula (I) where $R^4$ is a group $OCONR^{16}R^{17}$ may be prepared by a broadly similar method by reacting a compound of formula (VIIA)

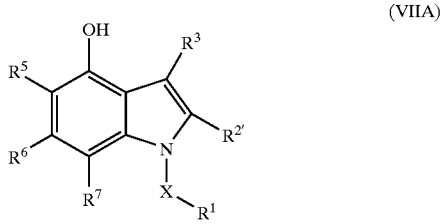

(VIIA)

where X, $R^{2'}$, R1, $R^3$, $R^5$, $R^6$ and $R^7$ are as defined in relation to formula (I), $R^2$ is a group $R^2$ as defined in relation to formula (I) or a protected form thereof, with a compound of formula (VIIA)

$$Z\text{—}CONR^{16}R^{17} \qquad \text{(VIIA)}$$

where Z, $R^{16}$ and $R^{17}$ are as defined above.

Compounds of formula (VIIA) can be prepared by reacting a compound of formula (IX)

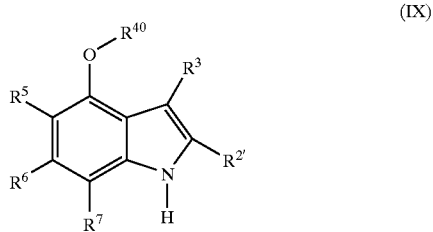

(IX)

where $R^3$, $R^5$, $R^6$ and $R^7$ are as defined in relation to formula (I) and $R^{2'}$ is as defined in relation to formula (VII) and $R^{40}$ is a protecting group; with compound of formula (X)

$$R^1\text{—}X\text{—}Z^1 \qquad \text{(X)}$$

where $R^1$ and X are as defined in relation to formula (I) and $Z^1$ is a leaving group, and thereafter, removing the protecting group $R^{40}$.

Suitable leaving groups for Z include halide such as chloride, bromide or iodide, as well as mesylate or tosylate. The reaction is suitably effected in an organic solvent such as dimethylformamide (DMF) tetrahydrofuran (THF) or DCM in the presence of a base such as sodium hydride, sodium hydroxide, potassium carbonate. Optionally the reaction is effected in the presence of a suitable phase transfer catalyst. The choice of base and solvent is interdependent to a certain extent in that certain solvents are compatible with some bases only as is understood in the art.

For example, sodium hydride may preferably be used with dimethylformamide or tetrahydrofuran and sodium hydroxide is preferably used with dichloromethane and a phase transfer catalyst.

The reaction can be carried out at moderate temperatures, for example from 0 to 50° C. and conveniently at about ambient temperature.

Preferably, $R^{2'}$ is an ester group in the compound of formula IX and this may be subsequently converted to an acid or to another ester or salt, by conventional methods later in the process. For example, when X is a group $SO_2$ and $R^2$ is a methyl ester of carboxy, it may be converted to the corresponding carboxylic acid by reaction with lithium iodide in dry pyridine or DMF.

Suitable protecting groups $R^{40}$ include acetyl or benzyl. The reaction conditions employed will be variable depending upon the nature of the protecting group $R^{40}$ and would be apparent to a skilled person. Acetyl groups may be removed by reaction with a strong base such as sodium methoxide, whereas benzyl groups may be removed by hydrogenation for example in the presence of a catalyst such as a palladium catalyst.

Compounds of formula (IX) may be prepared by cyclisation of a compound of formula (XII)

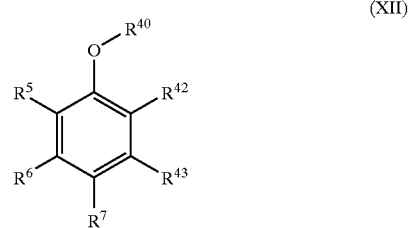

(XII)

where $R^5$, $R^6$, $R^7$ and $R^{40}$ are defined above and $R^{42}$ and $R^{43}$ represent a combination of moieties which can cyclise to form an appropriately substituted pyrrole ring. For example, one of $R^{42}$ and $R^{43}$ can be a group of formula —CH=C($R^{44}$)$N_3$ where $R^{44}$ is a group $R^2$ as defined above, or a protected form thereof, and the other may be hydrogen. Cyclisation to form a compound of formula (XII) may then be effected by heating for example under reflux in an organic solvent, in particular a high boiling aprotic solvent such as xylene or toluene.

Alternatively, one of $R^{42}$ and $R^{43}$ may be nitro and the other may be a group of formula —$CH_2C(O)R^{2'}$ where $R^{2'}$ is as defined above in relation to formula (VII). These compounds will cyclise in the presence of a catalyst such as palladium on carbon in the presence of hydrogen. The reaction may be effected at moderate temperatures for example of from 0 to 80° C., conveniently at about ambient temperature.

Thus examples of compounds of formula (XII) include compounds of formula (XIII) and (XIV)

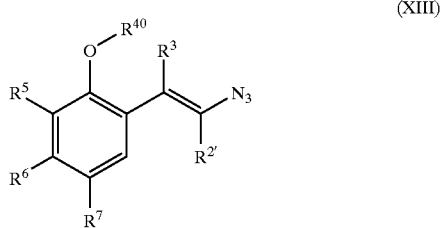

(XIII)

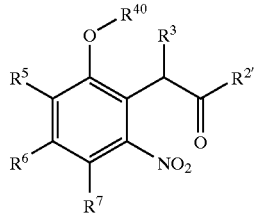

(XIV)

Compounds of formula (XIII) where $R^3$ is hydrogen may be prepared for example by reacting a compound of formula (XV)

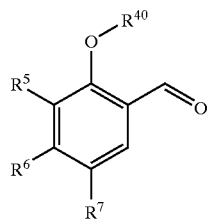

(XV)

with a compound of formula (XVI)

$$N_3CH_2R^{2'} \quad \text{(XVI)}$$

where $R^5$, $R^6$, $R^7$, and $R^{2'}$ are as defined hereinbefore. The reaction may be effected in an organic solvent such as ethanol at low temperatures of from −20 to 0° C., suitably at about 0° C. The reaction is suitably effected in the presence of a base such as an alkoxide, in particular an ethoxide, for example potassium ethoxide.

Compounds of formula (XVI) are suitably prepared by reacting a compound of formula (XVII)

$$R_{47}CH_2R^{2'} \quad \text{(XVII)}$$

where $R^{2'}$ is as defined above and $R^{47}$ is a leaving group such as halide and in particular bromide, with an azide salt, such as an alkali metal azide salt in particular sodium azide.

Compounds of formula (XIV) may be prepared by reacting a compound of formula (XVIII)

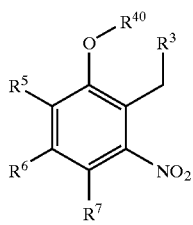

(XVIII)

where $R^5$, $R^6$, $R^7$, $R^3$, $R^{40}$ and $R^{2'}$ are as defined above, with a compound of formula (XIX)

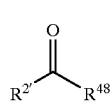

(XIX)

where $R^{2'}$ is as defined above and $R^{48}$ leaving group such as hydroxy. Examples of compounds of formula (XVI) are oxalates such as diethyloxalate. The reaction is suitably effected in the presence of a base such as sodium hydride in an organic solvent such as THF. Moderate temperatures of form 0° to 40° C. and conveniently ambient temperature is employed.

Compounds of formula (VII) are suitably prepared using a reaction analogous to that between compounds (IX) and (X), where in place of a compound of formula (IX), a compound of formula (IXA) is employed

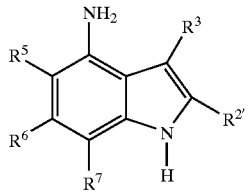

(IXA)

where $R^{2'}$, $R^3$, $R^5$, $R^6$ and $R^7$ are as defined above. Such compounds may be obtained by reduction of the corresponding nitro compound of formula (XX)

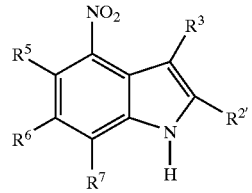

(XX)

where $R^{2'}$, $R^3$, $R^5$, $R^6$ and $R^7$ are as defined above.

Compounds of formula (X), (XVI), (XV), (XVII), (XVIII), (XIX) and (XX) are either known compounds or they may be prepared from known compounds by conventional literature methods.

According to a further aspect of the invention there is provided a compound of the formula (I) as defined herein, or a pharmaceutically acceptable salt or an in vivo/ hydrolysable ester thereof, for use in a method of treatment of the human or animal body by therapy. In particular, the compounds are used in methods of treatment of inflammatory disease.

According to a further aspect of the present invention there is provided a method for antagonising an MCP-1 mediated effect in a warm blooded animal, such as man, in need of such treatment, which comprises administering to said animal an effective amount of a compound of formula (I), or a pharmaceutically acceptable salt, or an in vivo hydrolysable ester thereof.

The invention also provides a pharmaceutical composition comprising a compound of formula (I) as defined herein, or a pharmaceutically acceptable salt, or an in vivo hydolysable ester thereof, in combination with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administered by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phsophate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agent such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the return to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 mg of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and society and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 0.25 mg per kg body weight will be used. Oral administration is however preferred.

A further aspect of the invention comprises the use of a compound of formula (I) as defined above in the preparation of a medicament for the treatment of inflammatory disease.

The invention is further illustrated, but not limited by the following Examples in which the following general procedures were used unless stated otherwise.

Preparation 1
Ethyl N-(3,4-dichlorobenzyl)-4-nitroindole-2-carboxylate

Ethyl 4-nitroindole-2-carboxylate (26 g) [prepared according to S. M. Parameter et al. *J. Amer. Chem. Soc.*, 1958, 80, 4621], 3,4-dichlorobenzyl chloride (16 ml), potassium carbonate (17 g) and potassium iodide (2 g) in DMF (250 ml) were stirred at 60° C. for 2 hours. The reaction was concentrated in vacuo and the residue partitioned between water and dichloromethane. Iso-hexane was added to the combined organic extracts resulting in crystallisation of the product as yellow needles (39 g, 89%) NMR d ($CD_3SOCD_3$) 1.30 (t, 3H), 4.32 (q, 2H), 5.93 (s, 2H), 6.88 (dd, 1H), 7.18 (d, 1H), 7.52 (d, 1H), 7.56 (dd, 1H), 7.78 (s, 1H), 8.17 (m, 2H); M/Z (+)1395 ($MH^+$), 393.

Preparation 2
Ethyl N-benzyl-4-aminoindole-2-carboxylate

A mixture of ethyl 4-nitroindole-2-carboxylate (8.2 g), anhydrous potassium carbonate (6.0 g) and benzyl bromide (4.3 ml) in DMF (100 ml) was stirred at 50–60° C. for 2 hours. The solvent was evaporated in vacuo and the residue partitioned between dichloromethane and water (250 ml each); the organic layer was separated, dried ($MgSO_4$) and evaporated to give a yellow solid (12 g), which was dissolved in a mixture of tetrahydrofuran/ethanol (200 ml, 1:1) and stirred while adding a solution of sodium dithionite (26 g) in water (50 ml). The mixture was stirred for 1 hour at 25° C. and partitioned between dichloromethane and water (200 ml each), the organic layer was washed with water (100 ml) and dried ($MgSO_4$). Combined organic extracts were concentrated in vacuo and the residue purified by column chromatography using dichloromethane as eluent to give a the product as a brown solid (1.4 g, 14%); NMR d ($CD_3SOCD_3$) 1.28 (t, 3H), 4.27 (q, 2H), 5.57 (s, 2H), 5.73 (s, 2H), 6.22 (d, 1H), 6.62 (d, 1H), 6.95–7.05 (m, 3H), 7.15–7.30 (m, 3H), 7.60 (s, 1H).

Preparation 3
Ethyl N-(3,4-dichlorobenzyl)-4-nitroindole-2-carboxylate

Sodium hydroxide (3M, 20 ml) was added to a vigorously stirred solution of ethyl 4-nitroindole-2-carboxylate (4 g), 3,4-dichlorobenzyl chloride (4.73 ml) and tetra-n-butylammonium hydrogensulphate (0.2 g) in dichloromethane (60 ml). The reaction was stirred for 48 hours then partitioned between 2M HCl and dichloromethane. Combined organic extracts were dried ($MgSO_4$) and concentrated in vacuo and the residue purified by column chromatography using iso-hexane: 20% ethyl acetate as eluent to give the product as a yellow crystalline solid (5.26 g, 78%); NMR δ ($CD_3SOCD_3$) 1.3 (t, 3H), 4.3 (q, 2H), 5.95 (s, 2H), 6.9 (m, 1H), 7.6 (m, 4H), 8.2 (t, 2H); M/z (+) 393.3 ($M^+$).

Ethyl N-(3,4-dichlorobenzyl)-4-aminoindole-2-carboxylate

A solution of ethyl N-(3,4-dichlorobenzyl)-4-nitroindole-2-carboxylate (2.41 g) in tetrahydrofuran (100 ml) was stirred in the presence of titanium trichloride (15% aqueous solution, 50 ml) at room temperature overnight. The reaction was treated with 40% sodium hydroxide solution and extracted with 5% methanol in dichloromethane. Combined organic extracts were dried ($MgSO_4$) and concentrated in vacuo to give the product as a brown solid (1.98 g, 89%); NMR d ($CD_3SOCD_3$) 1.3 (t, 3H), 4.2 (q, 2H), 5.7 (s, 4H), 6.2 (d, 1H), 6.6 (d, 1H), 7.0 (m, 2H), 7.25 (m, 1H), 7.5 (d, 1H), 7.6 (m, 1H); M/z (+) 363.3 ($MH^+$).

Preparation 4
Ethyl 4-chloroacetamido-N-(3,4-dichlorobenzyl)indole-2-carboxylate Ethyl 4-amino-N-(3,4-dichlorobenzyl)indole-2-carboxylate (2.03 g), chloroacetyl chloride (0.5 ml) and triethylamine (4.0 ml) were stirred in dichloromethane (50 ml) for 16 hours. The reaction was washed with water, dried ($MgSO_4$) and concentrated in vacuo. The residue was triturated with toluene to give the product as a pale grey solid (1.61 g, 65%); NMR d ($CD_3SOCD_3$) 1.28 (t, 3H), 4.30 (q, 2H), 4.40 (s, 2H), 5.81 (s, 2H), 6.88 (dd, 1H), 7.30 (m, 3H), 7.50 (d, 1H), 7.76 (s, 1H), 7.78 (d, 1H), 10.19 (brs, 1H); M/z (−) 439 ($M^+$), 4.37.

EXAMPLE 1

Compound 2

Ethyl 4-chloroacetamido-N-(3,4-dichlorobenzyl)indole-2-carboxylate (0.15 g) and morpholic (2.0 ml) were dissolved in methoxyethanol (5.0 ml) and the reaction stirred for 72 hours. The reaction was then poured into water (100 ml) and the resulting solid filtered and dried in vacuo. The solid was dissolved in THF (2.5 ml) and methanol (2.5 ml), and to this was added NaOH (3M, 2.0 ml). The reaction was stirred for 16 hours, then concentrated. The residue was dissolved in water, and precipitated by dropwise addition of acetic acid. The resulting solid was filtered and dried in vacuo to give the title compound as a white solid (0.1 g, 63%, 2 steps); NMR d ($CD_3SOCD_3$) 2.58 (t, 4H), 3.29 (s, 2H), 3.65 (t, 4H), 5.82 (s, 2H), 6.90 (dd, 1H), 7.30 (m, 3H), 7.52 (m, 2H), 7.72 (d, 1H), 9.80 (s, 1H); M/z (−) 462 ($M^+$), 460, 418.

EXAMPLE 2

The procedure described in Example 1 above was repeated using the appropriate amines. Thus were obtained the compounds described below.

Compound 3

49% yield, 2 steps; NMR d ($CD_3SOCD_3$) 2.27 (s, 3H), 2.54 (t, 4H), 2.62 (t, 4H), 3.22 (s, 2H), 5.84 (s, 2H), 6.95 (dd, 1H), 7.22 (m, 2H), 7.33 (s, 1H), 7.41 (s, 1H), 7.50 (d, 1H), 7.72 (d, 1H), 9.75 (s, 1H); M/z (−) 475 ($M^-$), 473, 429, 109.

Compound 6

14% yield, 2 steps; M/z (−) 510 (M⁻), 508, 464.

EXAMPLE 3

Di-ester of Compound 8

Ethyl 4-chloroacetamido-N-(3,4-dichlorobenzyl)indole-2-carboxylate (0.4 g), glycine methyl ester hydrochloride (0.57 g) and triethylamine (1.25 ml) were dissolved in methoxyethanol (4.0 ml) and the reaction heated at 100° C. for 6 hours. The reaction was cooled and partitioned between water and ethyl acetate. Combined organic extracts were dried (MgSO$_4$) and concentrated and the residue purified by chromatography using toluene:ethyl acetate (1:1) as eluent to give the product, ethyl 4-[(N-(methoxycarbonylmethyl)glycyl)amino]-N-(3,4-dichlorobenzyl)indole-2-carboxylate, as a pale yellow solid (0.17 g, 38%); NMR d (CD$_3$SOCD$_3$) 1.28 (t, 3H), 3.44 (s, 2H), 3.50 (s, 2H), 3.63 (s, 3H), 4.28 (q, 2H), 5.82 (s, 2H), 6.88 (dd, 1H), 7.10–7.30 (m, 4H), 7.50 (d, 1H), 7.69 (s, 1H), 7.80 (dd, 1H), 10.00 (brs, 1H); M/z (+) 494, 492 (M⁺).

EXAMPLE 4

Di-ester of Compound 11

Methanesulphonyl chloride (0.1 ml) was added to stirred solution of ethyl 4-[(N-(methoxycarbonylmethyl)glycyl)amino]-N-(3,4-dichlorobenzyl)indole-2-carboxylate (0.33 g) and triethylamine (0.47 ml) in dichloromethane (4.0 ml) and the reaction stirred for 3 hours. The reaction was poured into water and extracted with ethyl acetate. Combined organic extracts were dried (MgSO$_4$) and concentrated and the residue triturated with ether, filtered and dried in vacuo to give the product as a white solid (0.24 g, 63%); NMR d (CD$_3$SOCD$_3$) 1.27 (t, 3H), 3.10 (s, 3H), 3.67 (s, 3H), 4.20 (s, 2H), 4.28 (q+s, 2H+2H), 5.82 (s, 2H), 6.87 (dd, 1H), 7.28 (m, 3H), 7.50 (d, 1H), 7.80 (m, 2H), 10.00 (brs, 1H); M/z (+) 572, 570 (M⁺).

EXAMPLE 5

The procedure described in the Example 4 above was repeated using the appropriate acid chloride. Thus was obtained the compound described below.

Di-ester of Compound 12

64% yield; M/z (−) 534 (M⁺), 532.

EXAMPLE 6

Di-ester of Compound 14

Sarcosine ethyl ester hydrochloride (1.23 g) and potassium carbonate (1.11 g) were added to a solution of ethyl 4-chloroacetamido-N-(3,4-dichlorobenzyl)indole-2-carboxylate (700 mg) in acetone (25 ml), stirred and heated at 65° C. overnight. The reaction was partitioned between water (50 ml) and ethyl acetate (50 ml), extracted with ethyl acetate (2×50 ml), and dried (MgSO$_4$). The combined organic extracts were concentrated in vacuo, and the residue purified by column chromatography using 30% ethyl acetate: toluene as eluent, to afford the product as a yellow solid (768 mg, 92%); NMR d (CD$_3$SOCD$_3$) 1.21 (t, 3H), 1.28 (t, 3H), 2.45 (s, 3H), 3.42 (s, 2H), 3.53 (s, 2H), 4.16 (q, 2H), 4.30 (q, 2H), 5.81 (s, 2H), 6.88 (d, 1H), 7.27 (m, 2H), 7.52 (s, 1H), 7.67 (s, 1H), 7.84 (d, 1H), 9.95 (s, 1H), M/z(+) 520.3 (MH⁺)

EXAMPLE 7

The procedure described in Example 6 above was repeated using the appropriate amine. Thus was obtained the compound described below.

Diester of Compound 13

93% yield; NMR d (CD$_3$SOCD$_3$) 1.15 (t, 3H), 1.28 (t, 3H), 3.52 (s, 3H), 3.57 (s, 3H), 3.87 (s, 2H), 4.10 (q, 2H), 4.31 (q, 2H), 5.83 (s, 2H), 6.90 (d, 1H), 7.15–7.44 (m, 8H), 7.53 (d, 1H), 7.67 (s, 1H), 7.83 (d, 1H); M/z(+) 596.5 (MH⁺).

EXAMPLE 8

Di-ester of Compound 15

A solution of methyl iodide (0.026 ml) in DMF (2 ml) was added to a solution of sodium hydride (15 mg, 60% in mineral oil) and ethyl 4-[(N-benzyl-N-ethoxycarbonylmethyl)glycyl]amino-N-(3,4-dichlorobenzyl)indole-2-carboxylate (the diester of Compound 13) (200 mg) in DMF (4 ml), and stirred under an atmosphere of argon at ambient temperature for 4 hours. The reaction was quenched with water (50 ml) and extracted with ethyl acetate (3×50 ml), and the combined organic extracts were dried (MgSO$_4$), and concentrated in vacuo to afford the product as a pale brown oil (93 mg, 45%); NMR d (CD$_3$SOCD$_3$) 1.05 (t, 3H), 1.30 (t, 3H), 3.21 (s, 2H), 3.28 (s, 3H), 3.41 (s, 2H), 3.70 (s, 2H), 3.93 (q, 2H), 4.30 (q, 2H), 5.84 (s, 2H), 6.90 (d, 1H), 7.01 (d, 1H), 7.07–7.40 (m, 8H), 7.48–7.64 (m, 2H); M/z (+) 610.5 (MH⁺).

EXAMPLE 9

Compound 8

Ethyl 4-[(N-(methoxycarbonylmethyl)glycyl)amino]-N-(3,4-dichlorobenzyl)indole-2-carboxylate (0.15 g) was dissolved in THF/methanol (1:1) (10 ml) and sodium hydroxide (2M, 2.5 ml) was added and the reaction stirred for 16 hours. The reaction was then concentrated in vacuo and the residue dissolved in water. The solution was acidified by dropwise addition of acetic acid, resulting in the preparation of a white solid which was filtered, washed with water and dried in vacuo to give the desired end product as a white solid (108 mg, 79%); NMR d (CD$_3$SOCD$_3$) 3.40 (s, 2H), 3.64 (s, 2H), 5.82 (s, 2H), 6.92 (dd, 1H), 7.20–7.38 (m, 3H), 7.50 (d, 1H), 7.62 (s, 1H), 7.78 (d, 1H), 10.15 (brs, 1H).

EXAMPLE 10

The procedure described in Example 9 above was repeated using the appropriate ester. Thus were obtained the compounds described below.

Compound 11

79% yield; NMR d (CD$_3$SOCD$_3$) 3.10 (s, 3H), 4.02 (s, 2H), 4.20 (s, 2H), 5.83 (s, 2H), 6.88 (dd, 1H), 7.25 (m, 3H), 7.50 (d, 1H), 7.75 (s, 1H), 7.80 (d, 1H), 10.49 (brs, 1H); M/z (−) 528 (M⁺), 526, 360, 358, 289, 253, 217.

Compound 12

78% yield; NMR d (CD$_3$SOCD$_3$) 2.00 (d, 3H), 4.03 (s, 1H), 4.20 (s, 1H), 4.23 (s, 1H), 4.40 (s, 1H), 5.82 (s, 2H), 6.88 (m, 1H), 7.25 (m, 3H), 7.52 (dd, 1H), 7.76 (m, 2H), 10.13 (brs, 1H); M/z (−) 492 (M⁺), 490, 324, 253, 224.

Compound 14

60% yield; NMR d (CD$_3$SOCD$_3$) 2.46 (s, 3H), 3.38 (s, 2H), 3.42 (s, 2H), 5.88 (s, 2H), 6.92 (d, 1H), 7.20 (m, 2H), 7.31 (s, 1H), 7.50 (m, 2H), 7.82 (d, 1H); M/z (−) ) 462.2 (M–H⁺).

Compound 15

15% yield; NMR d (CD$_3$SOCD$_3$) 3.21 (s, 2H), 3.31 (s, 3H), 3.40 (s, 2H), 3.69 (s, 2H), 5.83 (s, 2H), 6.90 (d, 2H), 6.98 (d, 2H), 7.15 (m, 6H), 7.27 (t, 1H), 7.39 (s, 1H), 7.53 (m, 2H); M/z (−) 554.3 (M–H⁺).

Compound 13

25% yield; NMR d (CD$_3$SOCD$_3$) 3.44 (s, 2H), 3.46 (s, 2H), 3.85 (s, 2H), 5.91 (s, 2H), 6.87 (m, 1H), 7.13–7.36 (m, 6H), 7.40 (m, 2H), 7.53 (m, 2H), 7.78 (d, 1H), M/z (−) 538.2 (M−H$^+$), 253.2.

EXAMPLE 11

N-Benzyl-4-(2-pyrid-2-yl)thiophene-5-sulphonyl)(aminoindole-2-carboxylic acid (Compound 1)

To a solution of ethyl N-benzyl-4-aminoindole-2-carboxylate (140 mg) and pyridine (0.08 ml) in dichloromethane (10 ml) at 20° C. was added 2-(pyrid-2-yl)thiophene-5-sulphonyl chloride (140 mg) and the reaction stirred for 2 hours. The mixture was washed with HCl (2M, 10 ml), the organic layer was concetrated in vacuo and the residue purified by chromatography on silica using ethyl acetate as eluent, to give a yellow solid which was dissolved in ethanol (50 ml) at 60° C. and treated with NaOH (2M, 4.0 ml) with sirring for 2 hours. The solvent was evaporated in vacuo, the residue dissolved in water (50 ml) and filtered. The clear yellow filtrate was acidified with 2N HCl and extracted with dichloromethane/methanol (9:1, 100 ml). The organic layer was dried (MgSO$_4$) and evaporated to give a pale brown solid, which was triturated with ether to give the product as an off white powder (150 mg, 63%, 2 steps); NMR d (CD$_3$SOCD$_3$) 5.87 (s, 2H), 6.9–7.1 (m, 9H), 7.30 (dd, 2H), 7.43 (d, 1H), 7.63 (d, 1H), 7.81 (dd, 1H), 7.96 (d, 1H), 8.50 (d, 1H); M/z (−) 488 (M−H$^+$).

Example 12

The procedure described in Example 11 above was repeated using the appropriate aminoindole and sulphonyl chloride. Thus were obtained the compounds described below.

4-(4-Acetylaminobenzenesulphonyl)amino-N-(3,4-dichlorobenzyl)indole-2-carboxylic acid (Compound 4)

66% yield (2 steps); NMR d (CD$_3$SOCD$_3$) 2.00 (s, 3H), 5.75 (s, 2H), 6.80 (dd, 1H), 6.92 (d, 1H), 7.12 (dd, 1H), 7.22 (m, 2H), 7.48 (d, 1H), 7.56 (s, 1H), 7.66 (s, 4H), 10.24 (brs, 1H), 10.45 (brs, 1H); M/z (−) 532 (M−H$^+$), 530.

N-(3,4-Dichlorobenzyl)-4-(2-(pyrid-2-yl)thiophen-5-sulphonyl)aminoindole-2-carboxylic acid (Compound 5)

69% yield (2 steps); NMR d (CD$_3$SOCD$_3$) 5.80 (s, 2H), 6.80 (dd, 1H), 7.0–7.5 (m, 8H), 7.68 (d, 1H), 7.83 (dd, 1H), 7.92 (d, 1H), 8.48 (dd, 1H); M/z (−) 558 (M−H$^+$), 556.

N-(3,4-Dichlorobenzyl)-4-(1-methylimidazole-4-sulphonyl)aminoindole-2-carboxylic acid (Compound 7)

66% yield (2 steps); NMR d (CD$_3$SOCD$_3$) 3.60 (s, 3H), 5.78 (s, 2H), 6.86 (dd, 1H), 7.04 (1H, d), 7.15 (dd, 1H), 7.20 (d, 1H), 7.30 (d, 1H), 7.50 (d, 1H), 7.68 (m, 2H), 7.75 (s, 1H), 10.20 (brs, 1H); M/z (−) 479 (M−H), 477.

N-(3,4-Dichlorobenzyl)-4-(2-chloropyridyl-5-sulphonyl)aminoindole-2-carboxylic acid (Compound 9)

30% yield (2 steps); NMR d (CD$_3$SOCD$_3$)5.85 (s, 2H), 6.83 (d, 1H), 6.93 (dd, 1H), 7.03 (dd, 1H), 7.15 (d, 1H), 7.20 (s, (1H), 7.26 (s, 1H), 7.46 (d, 1H), 7.60 (d, 1H), 8.05 (dd, 1H), 8.62 (d, 1H); M/z (−) 512 (M−H$^+$), 510, 508.

EXAMPLE 13

Methyl N-(3,4-dichlorobenzyl)-4-(dimethylcarbamyloxy)indole-2-carboxylate (Methyl ester of Compound 10)

Dimethylcarbamyl chloride (83 mg) was added to a stirred solution of methyl N-(3,4-dichlorobenzyl)-4-hydroxyindole-2-carboxylate (150 mg), triethylamine (65 mg) and DMAP (5 mg) in dichloromethane. The reaction was stirred for 16 hours at room temperature under an atmosphere of nitrogen. The reaction was washed with hydrochloric acie (2M, 70 ml), saturated aqueous sodium hydrogencarbonate solution, water and saturated sodium chloride solution. Combined organic extracts were dried (MgSO$_4$), concentrated in vacuo and the residue purified by column chromatography using 60% ethyl acetate:iso-hexane as eluent to give the product as a colourless gum (132 mg,74%); NMR d (CD$_3$SOCD$_3$) 2.94 (s, 3H), 3.12 (s, 3H), 3.81 (s, 3H), 5.82 (s, 2H), 6.91 (m, 2H), 7.21 (s, 1H), 7.27–7.36 (m, 2H), 7.46 (d, 1H), 7.52 (d, 1H); M/z (+) 421 (MH$^+$).

EXAMPLE 14

N-(3,4-Dichlorobenzyl)-4-(dimethylcarbamyloxy)indole-2-carboxylic acid (Compound 10)

Desesterifiation of the compound of Example 13 using the method described in Example 9 above yielded Compound 10.

93% yield; NMR d (CD$_3$SOCD$_3$) 2.94 (s, 3H), 3.11 (s, 3H), 5.91 (s, 2H), 6.82 (d, 1H), 6.94–7.03 (m, 2H), 7.18 (t, 1H), 7.29–7.39 (m, 2H), 7.50 (d, 1H); M/z (−) 405 (M−H$^+$).

EXAMPLE 15

Biological Assays for hMCP-1 Antagonists

The following biological test methods, data and Examples serve to illustrate the present invention.

Abbreviations:

ATCC American Type Culture Collection, Rockville, USA.

BCA Bicinchroninic acid, (used, with copper sulphate, to assay protein)

BSA Bovine Serum Albumin

DMEM Dulbecco's modified Eagle's medium

EGTA Ethylenebis(oxyethylenenitrilio)tetraacetic acid

FCS Foetal calf serum

HEPES (N-[2-Hydroxyethyl]piperazineN'-[2-ethanesulphonic acid])

HBSS Hank's Balanced Salt Solution hMCP-1 Human Monocyte Chemoattractant Protein-1

PBS Phosphate buffered saline

PCR Polymerase chain reaction

AMPLITAQ™, available from Perkin-Elmer Cetus, is used as the source of thermostable DNA polymerase.

Binding Buffer is 50 mM HEPES, 1 mM CaCl$_2$, 5 mM MgCl$_2$, 0.5% foetal calf serum, adjusted to pH 7.2 with 1 M NaOH.

Non-Essential Amino Acids (100× concentrate) is: L-Alanine, 890 mg/l; L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt): 5000 units/ml: Streptomycin sulphate, 5000 µg/ml.

Human monocytic cell line THP-1 cells are available from ATCC, accession number ATCC TIB-202.

Hank's Balanced Salt Solution (HBSS) was obtained from Gibco; see *Proc. Soc. Exp. Biol. Med.,* 1949, 71, 196.

Synthetic cell culture medium, RPMI 1640 was obtained from Gibco; it contains inorganic salts [Ca(NO$_3$)$_2$.4H$_2$O 100 mg/l; KCl 400 mg/l; MgSO$_4$.7H$_2$O 100 mg/l; NaCl 6000 mg/l; NaHCO$_3$ 2000 mg/l & Na$_2$HPO$_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)- ethane-N,N,N', N'-tetraacetic acid pentaacetoxymethyl ester and was obtained from Molecular Probes, Eugene, Oreg., USA.

Blood Sedimentation Buffer contains 8.5 g/l NaCl and 10 g/l hydroxyethyl cellulose.

Lysis Buffer is 0.15M $NH_4Cl^-$, 10 mM $KHCO_3$, 1 mM EDTA

Whole Cell Binding Buffer is 50 mM HEPES, 1 mM $CaCl_2$, 5 mM $MgCl_2$, 0.5% BSA, 0.01% $NaN_3$, adjusted to pH 7.2 with 1M NaOH.

Wash buffer is 50 mM HEPES, 1 mM $CaCl_2$, 5 mM $MgCl_2$, 0.5% heat inactivated FCS, 0.5M NaCl adjusted to pH7.2 with 1M NaOH.

General molecular biology procedures can be followed from any of the methods described in "Molecular Cloning—A Laboratory Manual" Second Edition, Sambrook, Fritsch and Maniatis (Cold Spring Harbor Laboratory, 1989).

i) Cloning and expression of hMPC-1 receptor

The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci USA*, 91, 2752). The resulting PCR products were cloned into vector PCR-II™ (In Vitrogen, San Diego, Calif.). Error free CCR2B cDNA was subcloned as a Hind III-Not I fragment into the eukaryotic expression vector pCDNA3 (In Vitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell,* 16, 777). Transfected cells were selected by the addition of Geneticin Sulphate (G418, Gibco BRL) at 1 mg/mlo, 24 hours after the cells had been transfected. Preparation of RNA and Norther Blotting were carried out as described previously (Needham et al., 1995, *Prot. Express. Purific.*, 6, 134). CHO-K1 clone 7 (CHO-CCR2B) was identified as the highest MCP-1 receptor B-expressor.

ii) Preparation of membrane fragments

CHO-CCR2B cells were grown in DMEM supplemented with 10% foetal calf serum, 2 mM glutamin, 1× Non-Essential Amino Acids, 1× Hypoxanthine and Thymidine Supplement and Penicillin-Streptocymin (at 50 µg streptomycin/ml. Giboc BRL). Membarane fragments were prepared using cell lysis/differential centrifugation methods as described previously (Siciliano et al., 1990, *J. Biol. Chem.*, 265, 19658). Protein concentration was estimated by BCA protein assay (Pierce, Rockform, Ill.) according to the manufacturer's instructions.

iii) Assays $^{125}I$ MCP-1 was preapred using Bolton and Hunter conjugation (Bolton et al., 1973, *Biochem. J.*, 133, 529; Amersham International plc]. Equilibrium binding assays were carried out using the method of Ernst et al., 1994, *J. Immunol.*, 152, 3541. Briefly, varying amounts of $^{125}I$-labeled MCP-1 were added to 7 µg of purified CHO-CCR2B cell membranes in 100 µl of Binding Buffer. After 1 hour incubation at room temperature the binding reaction mixtures wre filtered and washed 5 times through a plate washer (Brandel MLR-96T Cell Harvester) using ice cold Binding Buffer. Filter mats (Brandel GF/B) were pre-soaked for 60 minutes in 0.3% polyethyleneimine prior to use. Following filtration individual filters were separated into 3.5 ml tubes (Sarsted No. 55.484) and bound $^{125}I$-labeled MCP-1 was determined (LKB 1277 Gammamaster). Cold competition studies were performed as above using 100 pM $^{125}I$-labeled MCP-1 in the presence of varying concentrations of unlabelled MCP-1. Non-specific binding was determined by the incinsion of a 200-fold molar excess of unlabelled MCP-1 in the reaction.

Ligand binding studies with membrane fragments prepared from CHO-CCR2B cells showed that the CCR2B receptor was present at a concentration of 0.2 pmoles/mg of membrnae protein and bound MCP-1 selectively and with high affinity ($IC_{50}$=110 pM, $K_d$=120 pM). Binding to these membranes were completely reversible and reached euqilibrium after 45 minutes at room temperature, and there was a linear relationship between MCP-1 binding and CHO-CCR2B cell membrane concentration when using MPC-1 at concentrations between 10 pM and 500 pM.

Test compounds dissolved in DMSO (5 µl) were tested in competition with 100 pM labelled CMP-1 over a concentration range (0.01–50 µM) in duplicate using eight point dose-response curves and $IC_{50}$ concentrations were calculated.

Compounds tested of the present invention had $IC_{50}$ values of 500 µM or less in the hMCP-1 receptor binding assay described herein. For example Compound 2 in Table 1 showed $IC_{50}$ of 1.7 µM in hMCP-1.

b) MCP-1 mediated calcium flux in THP-1 cells

The human monocytic cell line THP-1 was grown in a synthetic cell culture medium RPMI 1640 supplemented with 10% foetal calf serum, 6 mM glutamine and Penicillin-Streptomycin (at 50 µg streptomycin/ml, Gibco BRL). THP-1 cells were washed in HBSS (lacking $Ca^{2+}$ and $Mg^{2+}$)+1 mg/ml BSA and resuspending in the same buffer at a density of 3×10$^6$ cells/ml. The cells were then loaded with 1 mM FURA-2/AM for 30 min at 37° C., washed twice in HBSS, and resuspended in 1×10$^6$ cells/ml. THP-1 cell suspension (0.9 ml) was added to a 5 ml disposable curvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophootmeter (Perkin Elmer, Norwalk, Conn.) and pre-incubated for 4 min at 37° C. with stirring. Fluorescence was recorded over 70 sec and cells wre stimulated by addition of hMCP-1 to the curvette after 10 sec. $[Ca^{2+}]i$ was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic $[Ca^{2+}]$ according to the equation:

$$[Ca^{2+}]i=K_d(R-Rmin)(Sf2/Sb2)/(Rmax-R)$$

where the $K_d$ for FURA-2 $Ca^{2+}$ complex at 37° C. was taken to be 244 nm. $R_{max}$ is the maximal fluorescence ratio determined after additional of 10 mM lonomycin, $R_{max}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in $[Ca^{2+}]i$ in a speciifc and dose dependent manner. Dose response curves indicated an approixmate $EC_{50}$ of 2 nm. Test compounds dissolved in DMSO (10 µl) were assayed for inhibition of calcium release by adding them to the cell suspension 10 sec prior to ligand addition and measuring the reduction in the tranient size $[Ca^{2+}]i$. Test comounds were also checked for lack of agonist activity by addition in place of hMCP-1.

c) hMCP-1 and RANTES mediated chemotaxis.

In vitro chemotaxis assays were performed using the human monocytic cell line THP-1. Cell migration through polycarbonate membranes was measured by enumerating those passing through either directly by Coulter counting or indirectly by use of a colourimetric viability assay measuring the cleavage of a tetrazolium salt by the microchondrial respiratory chain (Scudiero D. A. et al. 1988, *Cancer Res.,* 48, 4827–4833).

Chemoattractants were introduced into a 96-well microtiter plate which forms the lower well of a chemotaxis chamber fitted with a PVP-free 5 μm poresize polycarbonate adhesive framed filter membrane (NeuroProbe MB series, Cabin John, MD 20818, USA) according to the manufacturer's instructions. The chemoattractant was diluted as appropriate in synthetic cell culture medium, RPMI 1640 (Gibco) or supplemented with 2 mM glutamine and 0.5% BSA, or alternatively with HBSS with $Ca^{2+}$ and $Mg^{2+}$ without Phenol Red (Gibco) plus 0.1% BSA. Each dilution was degassed under vacuum for 30 min and was placed (400 μl) in the lower wells of the chamber and THP-1 cells ($5 \times 10^5$ in 100 μl RAMPI 1640+0.5% BSA) were incubated in each well of the upper chmaber. For the inhibition of chemotaxis the chemoattractant was kept at a constant submaximal concentration determined previously (1 nM MCP-1) and added to the lower well together with the test compound dissolved in DMSO (final DMSO concentration <0.05% v/v) at varying concentrations. The chamber was incubated for 2 h at 37° C. The medium was removed from the upper wells which were then washed out with 200 μl physiological saline before opening the chamber, wiping dry the membrane surface and centrifuging the 96 -well plate at 600 cookies for 5 min to harvest the cells. Supernatant (150 μl) was aspirated and 10 μl of cell proliferation reagent, WST-1, {4-[3-(4-iodophenyl)-2-(4-nitrophenyl)-2H-5-tetrazolio]-1, 3-phenyl disulfonate} plus an electron coupling reagent (Boehringer Mannheim, Cat.no. 1644 807) was added back to the wells. The plate was incubated at 37° C. for 3 h and the absorbance of the soluble formazan product was read on a microtiter plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcerin AM (Glycerine, N,N'-[[3',6'-bis(acetyloxy)-3-oxospir [isobenzofuran-1(3H), 9'-[9H]xanthene]-2.7 diyl]bis (methylene)] bis[N-2-[(acetyloxy)methoxy]-2-oxoethyl]]-bis [(acetyloxy)methyl] ester. Molecular Probes) for 45 minutes in the dark. Cells are harvested by centrifugation and resuspended in HBSS (without Phenol Red) with $Ca^{2+}$, $Mg^{2+}$ and 0.1% BSA. 50 μl (2×105 cells) of the cell suspension are placed on the filter above each well and, as above, the unit is incubated at 37° C. for 2 hours under 5% $CO_2$. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and $IC_{50}$ of compounds under test and significant tests can be calculated. In addition to MCP-1 induced chemotaxis, this alternative form of the assay was also used to measure inhibition of RANTES (2 nM) induced chemotaxis.

d) Binding to human peripheral blood mononucelar cells (PMBCs)

i) Preparation of human PBMCs

Fresh human blood (200 ml) was obtained from volunteer donors, collected into sodium citrate anticoagulant to give a final concentration of 0.38%. The blood was mixed with Sedimentation Buffer and incubated at 37° C. for 20 minutes. The supernatant was collected and centrifuged at 1700 rpm for 5 minutes (Sorvall RT6000D). The pellet obtained was resuspended in 20 ml RMPMI/BSA (1 mg/ml) and 4×5 mls of cells were carefully layered over 4×5 mls of Lymophoprepä (Nycomed) in 15 ml centrifuge tubes. Tubes were spun at 1700 rpm for 30 minutes (Sorvall RT6000D) and the resultant layer of cells was removed and transferred to 50 ml Falcon tubes. The cells were washed twice in Lysis Buffer to remove any remaining red blood cells followed by 2 washes in RMPI/BSA. Cells were resuspended in 5 mls of Binding Buffer. Cell number was measured on a Coulter counter and additional binding buffer was added to give a final concentration of $1.25 \times 10^7$ PBMCs/ml.

ii) Assay

[$^{125}$I]MCP-1 was prepared using Bolton and Hunter conjugation (Bolton et al., 1973, *Biochem. J.,* 133: 529; Amersham International plc]. Equilibrium binding assays were carried out using the method of Ernest et al., 1994, *J. Immunol.,* 152, 3541. Briefly, 50 μl of $^{125}$I-labeled MCP-1 (final concentration 100 pM) was added to 40 μl ($5 \times 10^5$ cells) of cell suspension in a 96 well plate. Compounds, diluted in Whole Cell Binding Buffer from a solution of 10 mM in DSMO were added in a final volume of 5 μl to maintain a constant DMSO concentration in the assay of 5%. Total binding was determined in the absence of compound. Non-specific binding was defined by the addition of 5 μl cold MCP-1 to give a final assay concentration of 100 nM. Assay wells were made up to a final volume of 100 μl with Whole Cell Binding Buffer and the plates sealed. Following incubation at 37° C. for 60 minutes the binding reaction mixtures were filtered and washed for 10 seconds using ice cold Wash Buffer using a plate washer (Brandel MLR-96T Cell Harvester). Filter mats (Brandel GF/B) were pre-soaked for 60 minutes in 0.3% polyethylenimine plus 0.2% BSA prior to use. Following filtration individual filters were separated into 3.5 ml tubes (Sarstedt No. 55.484) and bound $^{125}$I -labeled MCP-1 was determined (LKB 1277 Grammamaster).

Test compound potency was determined by assay in duplicate using six point dose-response curves and $IC_{50}$ concentrations were determined.

Compound No. 13 in Table 1 showed 94% inhibition at 20 μm.

No physiologically unacceptable toxicity was observed at the effective dose for compounds tested of the present invention.

EXAMPLE 16

Pharmaceutical Compositions

The following Example illustrates, but is not intended to limit, pharmaceutical dosage forms of the invention as defined herein (the active ingredient being termed "Compound X"), for therapeutic or prophylactic use in humans:

| Tablet I | mg/tablet |
|---|---|
| (a) | |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| (b) | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| (c) | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| (d) | |
| Compound X | 10 |
| Lactose Ph.Eur | 488.5 |
| Magnesium | 1.5 |

| Injection I | (50 mg/ml) |
|---|---|
| (e) | |
| Compound X | 5.0% w/v |
| 1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

| Injection II | (10 mg/ml) |
|---|---|
| (f) | |
| Compound X | 1.0% w/v |
| Sodium phosphate BP | 3.6% w/v |
| 0.1M Sodium hydroxide solution | 15.0% v/v |
| Water for injection | to 100% |

| Injection III | (1 mg/ml, buffered to pH6) |
|---|---|
| (g) | |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

| Aerosol I | mg/ml |
|---|---|
| (h) | |
| Compound X | 10.0 |
| Sorbitan trioleate | 13.5 |
| Trichlorofluoromethane | 910.0 |
| Dichlorodifluoromethane | 490.0 |

| Aerosol II | mg/ml |
|---|---|
| (i) | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| Aerosol III | mg/ml |
|---|---|
| (j) | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| Aerosol IV | mg/ml |
|---|---|
| (k) | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| Ointment | ml |
|---|---|
| (l) | |
| Compound X | 40 mg |
| Ethanol | 300 µl |
| Water | 300 µl |
| 1-Dodecylazacycloheptan-2-one | 50 µl |
| Propylene glycol | to 1 ml |

Note:

Compound X in the above formulation may comprise a compound illustrated in Examples. The above formulations may be obtained by conventional procedures well know in the pharmaceutical art. The tables (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithinmay be replaced by an alternative suspending agent such as sorbital monooleate, sorbitan sesquinoleate, polysorbate 80, polyglycerol oleate or oleic acid.

What is claimed is:

1. A compound of formula (I)

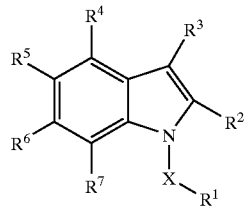

(I)

X is $CH_2$;

$R^1$ is an optionally substituted aryl;

$R^2$ is carboxy;

$R^3$ is halogen, optionally substituted alkyl, optionally substituted alkenyl, optionally substituted alkynyl;

$R^4$ is a group $NHSO_2R^{15}$ where $R^{15}$ is optionally substituted alkyl or optionally substituted aryl;

$R^5$, $R^6$ and $R^7$ are independently selected from hydrogen or an optionally substituted hydrocarbyl group.

2. A compound according to claim 1 wherein a group $R^{15}$ as it appears in the definition of $R^4$, is substituted by at least one functional group, or an aryl group, either of which may themselves be substituted by one or more functional groups or further aryl groups.

3. A compound according to claim 1 wherein $R^{15}$ is a substituted alkyl group or an optionally substituted phenyl group.

4. A compound according to claim 3 wherein $R^{15}$ is alkyl substituted by a group of formula $NR^{19}R^{20}$ where $R^{19}$ and $R^{20}$ are independently selected from hydrogen or optionally substituted hydrocarbyl.

5. A compound according to claim 1 wherein $R^1$ is 3,4-dichlorophenyl, 3-fluoro-4-chlorophenyl, 3-chloro-4-fluorophenyl or 2,3-dichloropyrid-5-yl.

6. A process for preparing a compound according to claim 1, which process comprises reacting a compound of formula (VII)

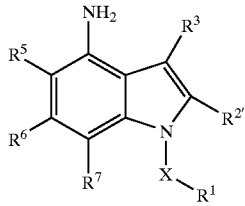

(VII)

where X, $R^1$, $R^3$, $R^5$, $R^6$ and $R^7$ are as defined in claim 1, and $R^2$ is a group $R^2$ as defined in relation to formula (I) or a protected form thereof, with a compound of formula (VIII)

$$Z-R^{22}$$ (VIII)

where Z is a leaving group and $R^{22}$ is a group $SO_2R^{15'}$ where $R^{15'}$ is group $R^{15}$ as defined in relation to formula (I) or a precursor thereof and thereafter is desired or necessary:

(i) converting a precursor group $R^{15'}$ to a group $R^{15}$ and/or converting a group $R^{15}$ to a different group $R^{15}$; and (ii) deprotecting a group $R^{2'}$ to a group $R^2$.

7. A pharmaceutical composition comprising a compound according to claim 1 in combination with a pharmaceutically acceptable carrier.

8. A method for treating inflammation in a warm blooded animal in need of such treatment comprising administering to said animal an effective amount of a compound according to claim 1, a pharmaceutically acceptable salt, or an in vivo hydrolysable ester thereof.

* * * * *

UNITED STATES PATENT AND TRADEMARK OFFICE
CERTIFICATE OF CORRECTION

PATENT NO.    : 6,911,465 B1
DATED         : June 28, 2005
INVENTOR(S)   : Faull et al.

It is certified that error appears in the above-identified patent and that said Letters Patent is hereby corrected as shown below:

Title page,
Item [75], Inventors, change "Allan W Faull" to -- Alan W. Faull --.

Column 1,
Line 17, change "astham" to -- asthma --;
Line 18, change "area" to -- areas --;
Line 42, after "is described" change "is" to -- in --;

Column 2,
Line 12, change "$(CH^{13})_3$" to -- $(CHR^{13})_r$ --;
Line 55, change "'aryl'" to -- 'alkyl' --;

Column 3,
Line 6, change "oxaxolyl, isoxaxolyl," to -- oxazolyl, isoxazolyl --;
Line 33, change "$R^2$" to -- $R^x$ --;
Line 34, change "$R^8$" to -- $R^x$ --;
Line 66, change "trifluoromethoxy," to -- trifluoromethyl --;

Column 4,
Line 4, change "$(C_{1-4}alkyl)_3$" to -- $C_{1-4}alkyl)_2$ --;
Line 8, change "-o($CH_2$)" to -- -O($CH_2$) --;
Line 13, change "3,4-fluoro" to -- 3-fluoro --;
Line 16, change "$SO_2H$" to -- $SO_3H$ --;
Line 21, change "$C_{1-7}$" to -- $C_{1-4}$ --;
Line 46, change "$(CHR^{22})$," to -- $(CHR^{22})_r$ --;

Column 6,
Line 5, change "$C_{1-8}$" to -- $C_{3-8}$ --;
Line 17, change "in-vivo" to -- in vivo --;

Column 8,
Line 31, change "$NHC(O)CH_2N(CH_3)CH_3COOH$" to
-- $NHC(O)CH_2N(CH_3)CH_2COOH$ --;

Column 12,
Line 3, change "form" to -- from --;
Line 39, change "vivo/" to -- vivo --;
Line 61, change "administered" to -- administration --;

Column 13,
Line 8, change "phsophate" to -- phosphate --;

UNITED STATES PATENT AND TRADEMARK OFFICE
CERTIFICATE OF CORRECTION

PATENT NO.   : 6,911,465 B1
DATED        : June 28, 2005
INVENTOR(S)  : Faull et al.

It is certified that error appears in the above-identified patent and that said Letters Patent is hereby corrected as shown below:

Column 14,
Line 30, change "return" to -- rectum --;

Column 15,
Line 10, delete "and society";
Line 36, change "S. M. Parameter et al." to -- S. M. Parmerter et al. --;
Line 46, change "M/Z (+)1395" to -- M/z(+)395 --;

Column 16,
Line 40, change "4.37" to -- 437 --;

Column 17,
Line 15, change "methyl)glycyl)" to -- methyl)-glycyl) --;
Line 66, change "7.25(s, 1H)" to -- 7.52(d, 1H) --;

Column 18,
Line 37, change "preparation" to -- precipitation --;
Line 66, change "M/z (-))" to -- M/z (-) --;

Column 19,
Line 51, change "(M-H)" to -- (M-H$^+$) --;

Column 20,
Line 54, change "salt):" to -- salt); --;

Column 21,
Line 34, change "mg/mlo" to -- mg/ml --;
Line 41, change "glutamin" to -- glutamine --;
Line 44, change "Giboc" to -- Gibco --;
Line 48, change "Rockform" to -- Rockford --;
Line 51, change "preapred" to -- prepared --;
Line 59, change "wre" to -- were --;
Line 62, change "polyethyleneimine" to -- polyethylenimine --;
Line 64, change "Sarsted" to -- Sarstedt --;

Column 22,
Line 2, change "incinsion" to -- inclusion --;
Line 7, change "membrnae" to -- membrane --;
Lines 9-10, change "euqi-librium" to -- equi-librium --;
Line 15, change "CMP-1" to -- MCP-1 --;
Line 37, change "spectrophootmeter" to -- spectrophotometer --;

UNITED STATES PATENT AND TRADEMARK OFFICE
CERTIFICATE OF CORRECTION

PATENT NO. : 6,911,465 B1
DATED : June 28, 2005
INVENTOR(S) : Faull et al.

It is certified that error appears in the above-identified patent and that said Letters Patent is hereby corrected as shown below:

Column 22 (cont'd),
Line 39, change "wre" to -- were --;
Line 51, change "$R_{max}$" to -- $R_{min}$ --;
Line 62, change "tranient size" to -- transient rise in --;

Column 23,
Line 4, change "microchondrial" to -- mitochondrial --;
Lines 7-8, change "micro-titer" to -- micro-titre --;
Line 19, change "RAMPI" to -- RPMI --;
Line 20, change "chmaber" to -- chamber --;
Line 23, change "compound" to -- compounds --;
Line 30, delete "cookies" and instead insert -- g --;
Line 47, change "Calcerin" to -- Calcein --;
Line 48, change "Glycerine" to -- Glycine --; and change "oxospir" to -- oxospiro --;

Column 24,
Line 5, change "(PMBCs)" to -- (PBMCs) --;
Line 14, change "RMPHI" to -- RPMI --;
Lines 15-16, change "Lymo-phoprepä" to -- Lym-phoprepä --;
Line 31, change "Ernst" to -- Emst --;
Line 32, change "$^{125}$-labeled" to -- $^{125}$I-labeled --;
Line 35, before "solution" insert -- stock --;

Column 27,
Line 10, change "lecithinmay" to -- lecinthin may --;
Line 12, change "sesquinoleate" to -- sesquioleate --; and
Line 30, change "halogen" to -- hydrogen --.

Signed and Sealed this

Eleventh Day of April, 2006

JON W. DUDAS
*Director of the United States Patent and Trademark Office*